United States Patent [19]
Castle

[11] Patent Number: 5,261,874
[45] Date of Patent: Nov. 16, 1993

[54] EXTRA-CORPOREAL BLOOD ACCESS, SENSING, AND RADIATION METHODS AND APPARATUSES

[75] Inventor: Kent D. Castle, Houston, Tex.

[73] Assignee: The United States of America as represented by the Administrator of the National Aeronautics and Space Administration, Washington, D.C.

[21] Appl. No.: 760,633

[22] Filed: Sep. 16, 1991

[51] Int. Cl.$^5$ .............................................. A61M 1/03
[52] U.S. Cl. ........................................ 604/4; 604/28
[58] Field of Search ........................... 604/4, 5, 6, 28; 128/362, 395, 399, 401

[56] References Cited

U.S. PATENT DOCUMENTS

| | | | |
|---|---|---|---|
| 3,484,369 | 12/1969 | De Dobbeleer | 210/22 |
| 3,799,672 | 3/1974 | Vurek | 356/41 |
| 3,851,181 | 11/1974 | Heule | 250/577 |
| 3,993,560 | 11/1976 | Halpern | 210/94 |
| 4,136,818 | 1/1979 | Larrabee | 233/1 R |
| 4,223,680 | 9/1980 | Jöbsis | 128/633 |
| 4,547,186 | 10/1985 | Bartlett | 604/4 |
| 4,619,640 | 10/1986 | Potolsky et al. | 604/7 |
| 4,737,140 | 4/1988 | Lee et al. | 604/4 |
| 4,787,883 | 11/1988 | Kroyer | 604/4 |
| 4,803,992 | 2/1989 | Lemelson | 128/634 |
| 4,820,260 | 4/1989 | Hayden | 604/4 |
| 4,867,738 | 9/1989 | Mintz | 604/4 |
| 4,895,558 | 1/1990 | Cham | 604/4 |
| 4,908,014 | 3/1990 | Kroyer | 604/4 |
| 4,948,248 | 8/1990 | Lehman | 356/40 |
| 4,950,225 | 8/1990 | Davidner et al. | 604/4 |
| 4,960,408 | 10/1990 | Klainer et al. | 604/4 |

OTHER PUBLICATIONS

"PDT Needs Better Lasers to Fulfill Its Promise," Pamela G. Goforth, Laser Focus World, Nov. 1990, p. 17.
"Fiberoptic Sources and Detectors Come of Age," Thomas V. Higgins, Laser Focus World, Nov. 1990, pp. 173-188.
"There is a lot more to an A-O Modulator than Meets the Eye," Thomas V. Higgins, Laser Focus World, Jul. 1991, pp. 133-143.
"Inactivation of Hepatitis Viruses and HIV in Plasma and Plasma Derivatives by Treatment with β-Propiolactone/UV Irradiation," W. Stephan, Current Studies in Hematologic Blood Transfusion, No. 56, 1989, pp. 122-127.
"In Vivo Activation by Ultraviolet Rays of the Human Immunodeficiency Virus Type 1 Long Terminal Repeat," vol. 86, Journal of Clinical Investigation, Oct. 1990, pp. 1369-1374.
"Medical Applications Call for Selectivity in Laser Performance," Marcia W. Patchan, Laser Focus World, Apr. 1991, pp. 85-104.
"Introduction of Expression of Human Immunodeficiency Virus in a Chronically Infested Promonocytic Cell Line by Ultraviolet Irradiation," Sharilyn K. Stanley, Thomas M. Folks, and Anthony S. Fauci, vol. 5, #4, 1989, Aids Research and Human Retroviruses, pp. 375-384.
"Echocardiography," Feigenbaum, pp. 7-11, 26-28 & 90, 1972.
"Ultrasound," ed. by Joyner, pp. 9-10, 16, & 146, 1974.
"Chromatic Structure Implicated in Activation of HIV-1 Gene Expression by Ultraviolet Light," Valerie et al, pp. 712-718, The New Biologist, vol. 2 #8, 1990.
"IEEE Guide for Medical Ultrasound Field Parameter Measurements," Institute of Electrical and Electronics Engineers, Inc., Jun. 29, 1990.

*Primary Examiner*—Robert A. Hafer
*Assistant Examiner*—Sam Rimell
*Attorney, Agent, or Firm*—Russell E. Schlorff; Guy M. Miller; Edward K. Fein

[57] ABSTRACT

Methods and apparatuses for extra corporeal access to blood for analysis of the blood and for treating it or constituents of it with force, energy, or radiation; e.g. electrical energy, heat, sound or electromagnetic or electrostatic force; such apparatuses in one aspect having one or more access ports in tubing or other members through which blood flows with treatment and/or analysis windows disposed at adjacent, within, or over the ports.

22 Claims, 4 Drawing Sheets

“EXTRA-CORPOREAL BLOOD ACCESS, SENSING, AND RADIATION METHODS AND APPARATUSES”

ORIGIN OF THE INVENTION

The invention described herein was made by an employee of the United States Government and may be manufactured and used by or for the Government of the United States of America for governmental purposes without the payment of any royalties thereon or therefor.

BACKGROUND OF THE INVENTION

1. Field Of The Invention

This invention is related to extra corporeal blood access and radiation methods and apparatuses and, in particular aspects, to such methods and apparatus in which flowing blood is subjected to energy in a variety of forms, including, but not limited to, radiation, electromagnetic force, fields or atomic particles.

2. Description Of Related Art

The prior art discloses a variety of methods for pumping blood to and from a blood source. In several of these methods blood is pumped from a person or animal, processed in some way, and then relatively quickly pumped back into the person's or animal's circulatory system.

For example, in both kidney dialysis and autologous blood transfusion methods, apparatuses are used which circulate a person's blood from the person's circulatory system to external processing apparatuses and then the processed blood is returned to the person's circulatory system.

The apparatuses involved in pumping and recirculating the blood employ tubing, pumps, connectors, seals, catheters, etc. to effectively and safely move and process blood.

Many medical techniques presently require that medication be taken orally and be processed through a patient's digestive and/or vascular system, or that medications be injected. Problems arise with each type of administration of medicine, including time to take effect and proper dosage. These methods may require multiple treatments. Recovery time associated with them may also be prolonged.

The prior art discloses a variety of blood analysis and treatment devices and methods. For example, U.S. Pat. No. 4,223,680 discloses a spectrophotometric method, apparatus, and reflectance technique which requires an interface with a part of a person's body and which monitors the metabolism of a body organ by measuring changes in the skin and blood. The measurements are made by transmitting near-infrared radiation to the organ, and then detecting and measuring the radiation intensity.

U.S. Pat. No. 4,803,992 discloses a medical instrument for viewing vascular system members internally and employs light energy and detects and measures body variables. The instrument has a catheter head structure containing optical components such as reflectors and lenses to detect such variables. The instrument detects specific elements or compositions and diagnoses various conditions and maladies.

U.S. Pat. No. 4,948,248 discloses a measuring device and method for determining concentration of constituents in the blood by measuring different absorption characteristics of different wavelengths of light as they are passed through living tissue containing blood. This reference specifically teaches a device which is less susceptible to the effect of electromagnetic waves.

U.S. Pat. No. 4,950,225 discloses a method for extra-corporeal blood treatment that includes subjecting at least a fraction of the blood to ultraviolet, x-ray, or laser radiation (See FIG. 4, items 172, 173, 174) and temperature adjustment of the blood by heating (Col. 10, lines 64–67) (See Col. 11, lines 25–68; Col. 12, lines 1–6).

U.S. Pat. No. 3,799,672 discloses a device for monitoring blood oxygen saturation during extra-corporeal bypass procedures and uses an infrared light emitting diode and a visible red light emitting diode to illuminate blood flowing through a plastic couvet. See Col. 3, lines 16–22; Col. 4, lines 54–68; Col. 6, lines 62–67).

U S. Pat. No. 4,737,140 discloses an extra-corporeal irradiation chamber and method for energizing photoactivatable substances in blood. (See FIG. 2 and Col. 3, lines 45–57).

U.S Pat. No. 4,787,883 discloses an extra-corporeal thermo-therapy device and method for continuously treating blood with separate blood heaters. U.S. Pat. No. 4,908,014 is a division of U.S. Pat. No. 4,787,883.

U.S. Pat. No. 3,851,181 discloses a blood level detector for monitoring blood levels with a light emitting element projecting through a transparent wall and light responsive elements receiving light reflected from the blood.

U.S. Pat. No. 4,960,408 discloses treatments and methods for stimulating immunological response in which a psoralen or furocoumarin compound in blood is activated by exposure to ultraviolet light.

U.S. Pat. No. 4,820,260 discloses a method and apparatus for sonication of blood to inactivate the sodium potassium ATPase of red blood cells in which the blood is subjected extra-corporeally to an ultrasound field.

U.S. Pat. No. 4,136,818 discloses a device for holding a transparent tube through which blood may flow and an optical sensor for detecting the presence of blood flow through the tube.

U.S. Pat. No. 3,993,560 discloses a method and apparatus for monitoring cellular activities that includes a technique for taking photographs through a transparent top or bottom cover of growing tissue.

U.S. Pat. Nos. 4,867,738; 4,895,558; 4,547,186; and 4,619,640 disclose a variety of transfusion systems.

"PDT Needs Better Lasers to Fulfill its Promise," P.G. Goforth, Laser Focus World, November 1990, page 17, describes photodynamic therapy and its applications. One application is the use of photosensitizing drugs and specific light wavelengths to eradicate cancer cells. A variety of light sources are discussed, including projectors and lasers.

"Fiberoptic Sources and Detectors Come of Age," T.V. Higgins, Laser Focus World, November 1990, page 173–188, discloses light sources for fiber optics and detectors employing them.

U.S. Pat. No. 3,484,369 discloses an apparatus for hemodialysis or artificial kidney with a plurality of blood flow conduits.

"There is a lot more to an A-O modulator than meets the eye," Laser Focus World, July 1991 describes acoustooptics in general.

"Inactivation of Hepatitis Viruses and HIV in Plasma and Plasma Derivatives by Treatment with B-Propiolactone/UV Irradiation," Current Studies in Hematologic Blood Transfusion, No. 56, 1989, pp. 122–127 describes the cold sterilization of plasma with a chemical agent and the photochemical sterilizing effect of ultraviolet radiation.

"In Viro Activation by Ultraviolet Rays of the Human Immunodeficiency Virus Type I Long Terminal Repeat," Vol. 86, Journal of Clinical Investigation, October 1990.

"Medical applications call for selectivity in laser performance," Laser Focus World April 1991, discusses, in general, medical applications of laser technology.

"Induction of Expression of Human Immunodeficiency Virus in a Chronically Infected Promonocytic Cell Line by Ultraviolet Irradiation," Stanley et. al, Vol. 5, Aids Research and Human Retroviruses, 1989, discusses inducing the expression of latent viruses with ultraviolet irradiation.

"Echocardiography," Feigenbaum, 1972, pages 7–11, 26–28, and 90 discuss medical ultrasound instrumentation and methods. Page 8 notes the absorption of ultrasound in blood.

"Ultrasound" ed. by Joyner, 1974, pp. 9–10, 16, 146 discusses medical ultrasound instrumentation.

"Chromatic Structure Implicated in Activation of HIV-1 Gene Expression by Ultraviolet Light," Valerie et. al, 1990, discusses DNA-damaging agents, e.g. ultraviolet light, and its effect on HIV-1 gene expression.

"IEEE Guide for Medical Ultrasound Field Parameter Measurements," Institute of Electrical and Electronics Engineers, Inc., Jun. 25, 1990 discusses in general hydrophones, radiation force, optics, and ultrasound detection and transmission.

SUMMARY OF THE PRESENT INVENTION

The present invention, in one embodiment, is directed to methods and apparatuses for accessing flowing blood and for subjecting the blood to electrical conductive, electrostatic or electromagnetic fields or for radiating the blood with some type of radiation, e.g. radiowaves, ultrasonic or audio waves, microwaves, infrared rays, visible light, ultraviolet radiation, X-rays, alpha, beta or gamma rays. In one aspect, an apparatus is employed which includes one or more access ports or windows for radiating blood and/or for sensing/analyzing blood. The ports are associated with windows made of appropriate material disposed on a tubing, chamber, or attached apparatus through which blood flows including, but not limited to, the tubing used in dialysis machines or autologous blood transfusion devices. According to certain embodiments of this invention, blood is thus radiated to treat a component of the blood with a certain radiation, to heat the blood, to change the blood or parts thereof, to sense and analyze the blood, to sense something in contact with the blood or blood stream with SONAR via audio, ultrasonic, or radio-frequencies, or to radiate some foreign organism or material in the blood. The access port(s) and access window(s) are located, configured and sized appropriately to facilitate the desired application of energy or radiation to the blood, its constituents, its interfaces or things therein.

In certain embodiments of the present invention, the blood, one or more of its constituents, or things therein (either naturally occurring or things injected into the blood, e.g. changed particles, etc.) are subjected to sound waves for examination including audio and ultrasonic sound waves applied through appropriate radiation ports and/or sensing-analysis windows. With certain of these embodiments, sonar-type mapping of the blood is possible.

In other embodiments, blood components are electrostatically charged for examination or for attracting one or more types of components to an object or to an area in a blood flow conduit. If undesirable material is charged, it can be attracted to a drain port area in the apparatus and removed from the blood stream. Other components may be charged for removal, removed, processed, and returned to the blood stream.

In another aspect, blood containing photodynamic material is subjected to light to activate the photodynamic material, including, but not limited to, laser beams, plasma light sources, multiple light sources and sun spectrum radiation.

To control the flow rate for radiation purposes, the access window area or the access port area may be restricted, elongated, enlarged, or altered so that a desired flow rate within a selected flow area is achieved. Atoms or accelerated particles e.g. but not limited to, atoms, X-rays, neutrons, protons, electrons, ions, alpha rays, beta rays, gamma rays may also be used to bombard blood. A wide range of radiation with different parameters may be employed, e.g. radiation of differing frequency, wavelength, intensity, and hue. Also, combinations of radiation sources and sensing/analysis ports and windows are possible. Electrical energy may be applied to the blood through an electrically conductive port or window or through multiple ports or windows. Electromagnetic fields may be imposed on the blood through a window, multiple windows, and related ports.

The present invention, therefore, is useful for, but not limited to: killing viruses in blood; killing bacteria in blood; monitoring blood for medical purposes; genetic modification of blood; and analyzing an/or treating blood components. The present invention teaches apparatuses and methods which are not invasive to the human or animal body, which do not require anesthesia, which provide access to the entire blood supply, and which can be implemented with existing blood processing devices, requiring little or no redesign. The present invention's apparatuses and methods are also useful with blood which is not being recirculated from a human or animal, but which can be pumped past an access port or access window. The methods and apparatuses according to the present invention can provide relatively quick treatment of a person's or animal's entire blood supply, blood components or a substantial part hereof.

In one embodiment according to the present invention, a window made of quartz, glass, plastic, metal or other suitable material is disposed across an access port opening provided in the existing flow tubing of a blood processing machine, such as a dialysis machine. Energy, e.g. radiation, is introduced through the window by a conventional energy source or radiation source, or transducer to treat the blood flowing through the tubing. In one aspect, additional treatment windows may be employed, either on the same tubing or elsewhere on the machine or on added apparatus, for treatment with similar or different energy or radiation or with a combination of different types of energies and/or different radiations. One or more additional windows may be employed with conventional sensors or sensing devices for sensing and analysis before, during, or after irradiation. In addition to use with dialysis machines, the present invention can be employed with machines that have a flow of a particular blood constituent, e.g. plasma. With appropriate radiation or electromagnetic force fields, the same window can be employed for both sensing/analysis and for treatment; e.g. light reflecting back to one or more microchips with the same port or window serving as both access port (for radiating the blood) and access window (for sensing-analysis).

The present invention recognizes and addresses a variety of needs and provides a satisfactory meeting of those needs in its various possible embodiments. To one of skill in this art who has the benefits of this invention's teachings and disclosures, further objects and advantages will be clear, as well as others inherent therein, from the following description of presently-preferred embodiments, given for the purpose of disclosure, when taken in conjunction with the accompanying drawings. Although these descriptions are detailed to ensure adequacy and to aid understanding, this is not intended to prejudice that purpose of this patent which is to claim an invention no matter how others may later disguise it by variations in form or additions of further improvements.

DESCRIPTION OF THE DRAWINGS

So that the manner in which the above-recited features, advantages, and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments. All views are schematic.

DESCRIPTION OF EMBODIMENTS PREFERRED AT THE TIME OF FILING FOR THIS PATENT

Figure 1:
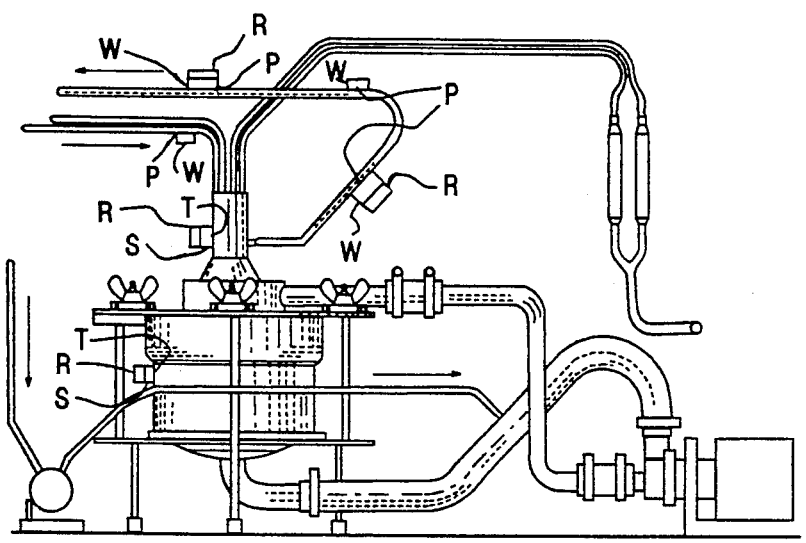
FIG. 1 is a perspective view of a blood processing machine with a system according to the present invention.

A dialysis machine M (as in U.S. Pat. No. 3,484,369) is shown in FIG. 1 with a plurality of access ports P and access windows W on its tubing according to this invention. Access ports T and access windows S are provided for access at points other than on the tubing. "R" signifies a conventional energy transducer and/or sensor used at a window to transmit or radiate energy into the flow stream or material and/or to sense energy/radiation reflected back from the stream.

Figure 2:
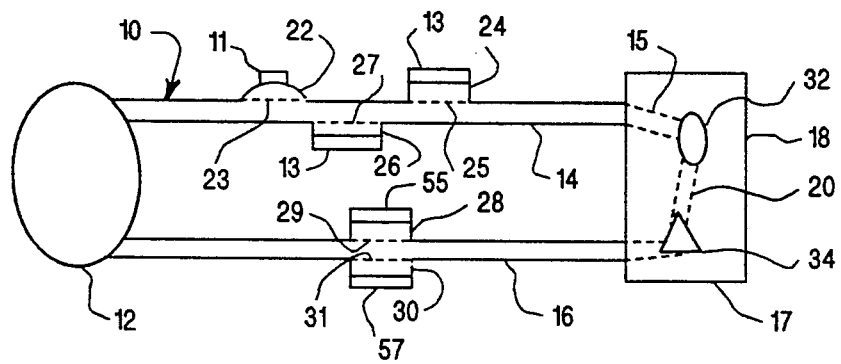
FIG. 2 is a schematic view of a system according to the present invention.

Referring now to FIG. 2, a system 10 according to the present invention pumps blood B from a blood source 12 (e.g. a human being or a blood storage container) through an outlet line 14, to and through an apparatus with a pump 18, and then via an inlet line 16 back to the blood source 12. A convex treatment window 22 made from quartz is disposed over an access port 23 in the tubing 14 through which treating force, energy or radiation from a source 11 using an appropriate transmission medium for the window and the related appropriate radiation may be directed to the blood or blood constituents flowing through the outlet line 14. As desired, a lens or lens system (of any lens configuration (e.g. convex, concave, plano-convex, etc.) may be used with a window or as a window.

Analysis windows 24 and 26 are over access ports 25 and 27 respectively on line 14. Sensors 13 are disposed at the windows 24, 26. Windows 32 and 34 in a housing 17 of apparatus with the pump 18 extend to tubing 15 which traverses the housing 17. These windows may be used for sensing-analysis, treatment, or both. Dual opposed windows 28 and 30 over access ports 29 and 31, respectively, in inlet line 16 permit the analysis or treatment of blood with energy source 55 and sensor 57, the blood being returned to the blood source 12. The designation "pump 18" may include apparatus that treats the blood or its constituents or that process the blood and/or separate it into its various components. The various access windows may then provide means for analyzing the blood before, during and after such treatment or processing. In another embodiment the items 55 and 57 represent electrical conductors between which electrical energy flows, the electrical energy flowing through the blood B that passes between items 55 and 57.

Figure 3:
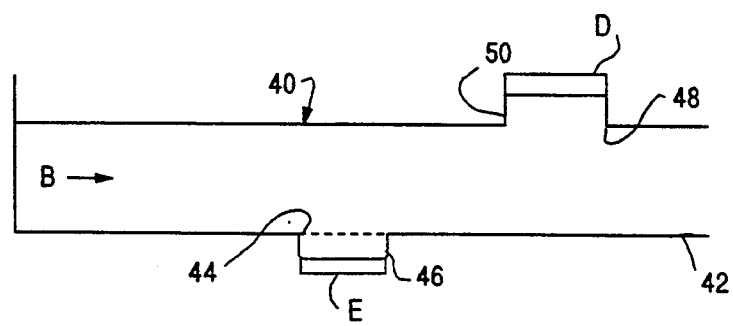
FIG. 3 is a side cross-sectional view of a device according to the present invention.

Referring now to FIG. 3, a system 40 according to this invention includes a blood conduit 42 through which blood B flows, the conduit 42 having a treatment window 46 over a conduit access port 44 and an analysis window 50 over an access port 48. With a suitable extraneous devise, any appropriate energy, radiation, audio or ultrasonic waves, electromagnetic fields or electrostatic fields may be applied to the blood from source E through the window 46. Similarly any appropriate sensing or analysis device D may interface with the window 50 to pass a ray or signal from the blood for analysis.

Figure 4:
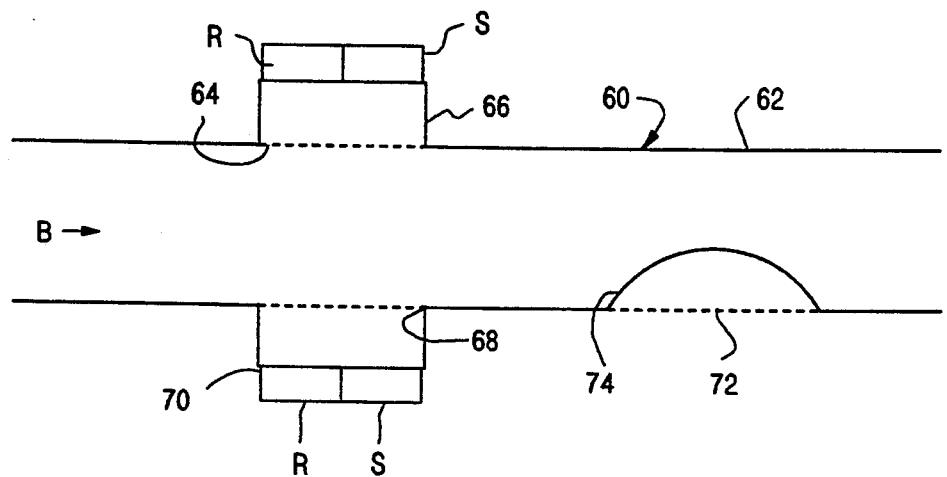
FIG. 4 is a side cross-sectional view of a device according to the present invention.

FIG. 4 illustrates a system 60 according to the present invention with a blood flow tubing 62 for blood B having dual opposed treatment windows 66 and 70 over tubing access ports 64 and 68 respectfully. An additional window 74 over an access port 72 is a planoconvex lens of appropriate radiation transmitting material with the convex portion of the lens projecting into the tubing 62. Energy sources R and/or sensors S adjacent both windows can be used, e.g., for blood treatment.

Blood flow rate is slower as the tubing increases in volume (e.g. adjacent windows 66 and 70), thus allowing longer access time in areas of increased volume. Similarly, shorter access time is made possible in areas of decreased volume (e.g. adjacent window 74) in which blood flow is faster for a constant volume of blood flow.

Figure 5:
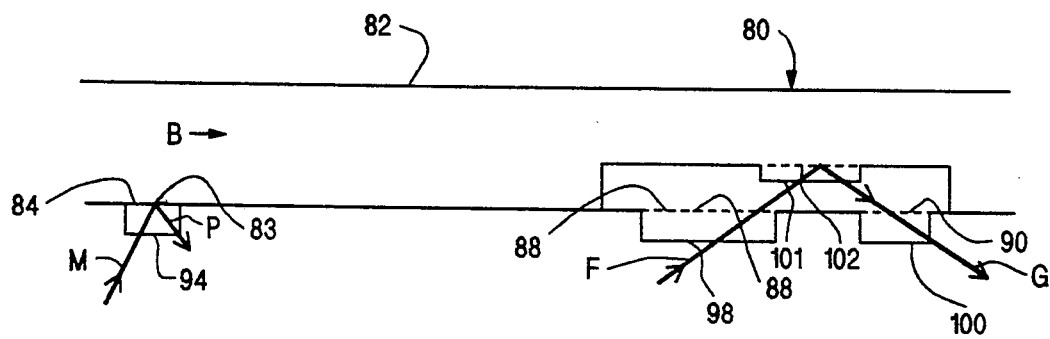
FIG. 5 is a side cross-sectional view of a device according to the present invention.

A system 80 according to the present invention, shown in FIG. 5, has a blood-flow line 82 for blood B with a window 94 and a corresponding line access port 84. Radiation, e.g. ray M, introduced through the window 94 is reflected back through the window 94, e.g. ray P. This reflection occurs at the surface of the blood 83 at which point radiation projected into the blood becomes a ray out from the blood which can be sensed for blood analysis. Such a configuration allows one port or window to be used in both radiation and sensing/analysis functions.

Radiation, e.g. ray F, may enter port 88 through window 98, travel to and through a window 101 at a port 102, and then be reflected, e.g. ray G, from the blood back through port 90 and window 100 which can be sensed for blood analysis. Previously described energy sources and/or sensors may be used adjacent the windows.

Figure 6:
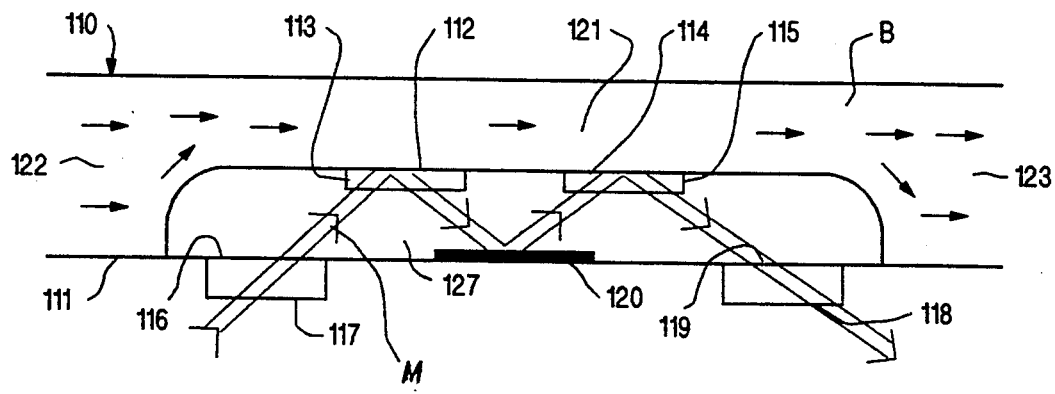
FIG. 6 is a side cross-sectional view of a device according to the present invention.

A system 110, according to the present invention shown in FIG. 6, has flow tubing 111 which is smaller in cross-sectional area (therefore increasing flow velocity) in a middle portion 121 than at ends 122 and 123, at a constant volume of flow. Arrows indicate flow direction. Radiation (exemplified by ray M from a conventional energy source) may enter through a window 117 at a port 116 and be directed through a transparent medium 127 at blood 122 flowing past a window 113 at a port 112. Part of the radiation R is reflected from the blood to a reflector member 120 which in turn directs radiation to the blood through the transparent medium and through a window 115 at a port 114. Finally, the radiation is then reflected from the blood 121 and through a window 118 at a port 119 for sensing and/or analysis with a conventional sensor/analyzer (not shown).

Figure 7:
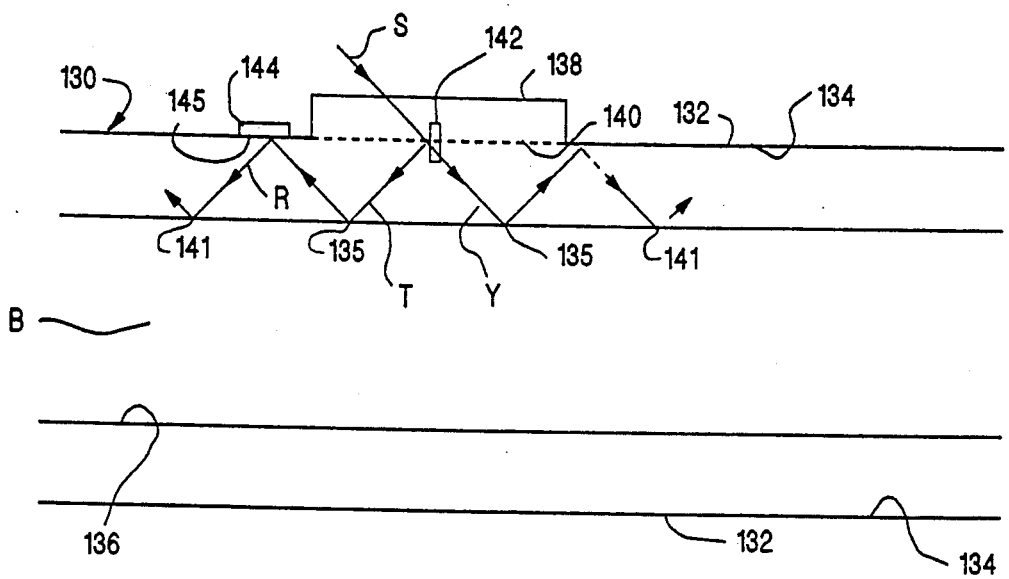
FIG. 7 is a side cross-sectional view of a device according to the present invention.

A system 130 shown in FIG. 7 has an outer tubing sheath 132 with an inner reflective coating or surface 134. Blood flows through inner transparent tubing 136. Radiation (exemplified by ray S) is directed through a window 138 by a conventional source (not shown) at a port 140 to, preferably a beam splitter 142 (e.g. a partially opaque mirror) and resulting rays T and V are then directed through the inner transparent tubing 136 to the blood B. Upon reflection from the blood B at 135, the rays encounter the reflective coating 134 and are subsequently reflected back to the blood B at 141. Multiple additional reflections are possible. Although a beam splitter is not required, it is preferred. Part of the rays are directed through a sensing-analysis window 144 at a port 145 and part of them (e.g. ray R) are reflected from the window.

Figure 8:
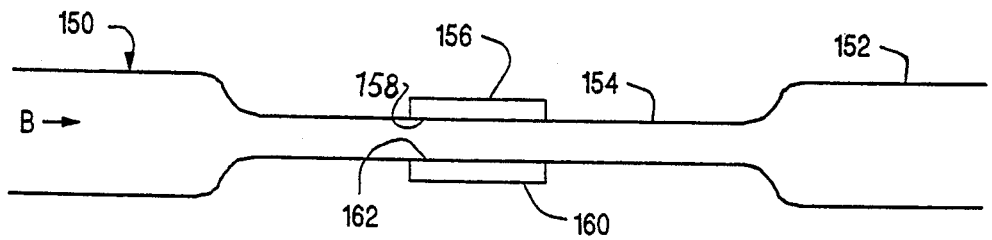
FIG. 8 is a side cross-sectional view of a device according to the present invention.

A system 150, according to the present invention shown in FIG. 8, has a flow tubing 152 with a relatively narrow portion 154. A window 156 at a port 158 is disposed opposite a window 160 at a port 162. The flow of blood B through the narrow portion 154 of the tubing is sufficiently thin that radiation may pass through the window 156, through the blood, and through the window 160 for sensing and/or analysis. Conventional energy sources and sensors (not shown) at the windows are used as previously described for other embodiments. A portion like portion 154 may be used with any embodiment disclosed herein.

Figure 9:
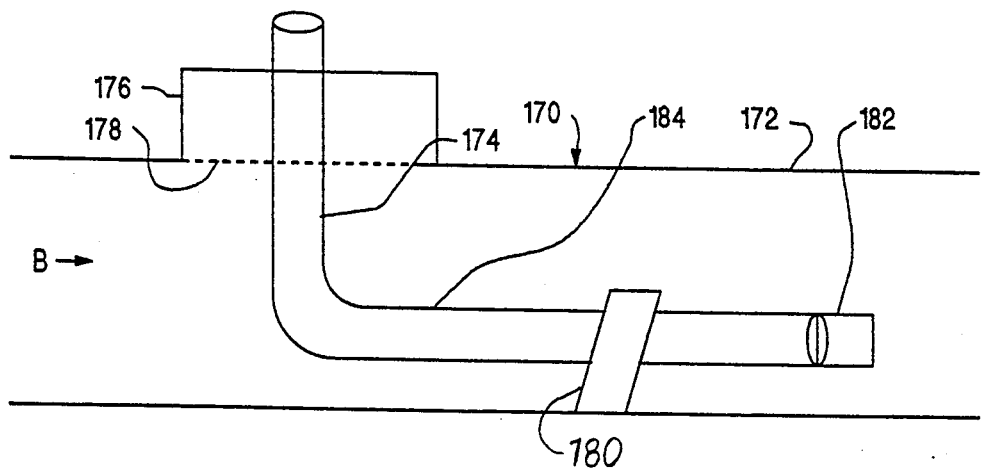
FIG. 9 is a side cross-sectional view of a device according to the present invention.

FIG. 9 illustrates another embodiment of the present invention. A system 170 includes tubing 172 through which blood or one or more blood constituents, B, flow. A light transmitting fiber optic cable 174 with one or more fiber optic strands therein extends through a window 176 and a port 178 in the tubing and into the flow stream within the tubing. If desired a bracket 180 may be used to stabilize the cable 174. A transducer 182 (which may also be a detector sensor) at the end of the cable converts modulation carried on light transmitted through the cable into audio, video, or pulse energy which is then radiated into the flow stream, thus nonmodulated light, modulated and/or demodulated energy is radiated into the stream. Opaque cladding 184 on the cable can be removed for additional light radiation of the stream. The cable need not extend through a window/port but may simply extend sealingly through a hole in the tubing. With or without the transducer 182 the system 170 may be used to heat the blood by sending appropriate radiant energy into the blood. Similarly the other systems described herein may be used to heat the blood.

It is to be understood that a reference in the claims to blood means whole blood or a stream of one or more blood constituents or items or particles in the blood.

In using SONAR techniques according to preferred embodiments of this invention, ultrasonic waves or radio-frequency waves are introduced into the blood at one point, e.g. through one of the windows in a system according to this invention as described herein and then at that window or at another point in the blood or another window, the reflection of those waves from an item in or in contact with the blood is sensed and/or analyzed, e.g. by a hydrophone sensor in the blood stream. Thus extra-corporeal SONAR mapping of blood is possible with this invention.

Figure 10:
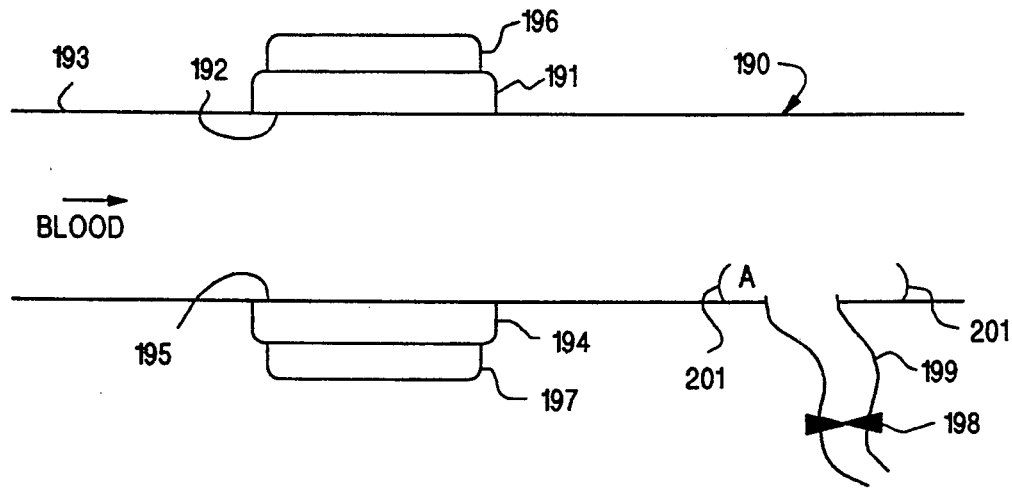
FIG. 10 is a side cross-sectional view of a device according to the present invention.

As shown in FIG. 10, a system 190 may be employed to electrostatically charge blood or items or particles in blood and to remove such charged items or particles. A window 191 at port 192 on one side of a blood flow conduit 193 is disposed opposite another Window 194 at a port 195 on the conduit. A charging device with components 196 (at window 191) and 197 (at window 194) induces an electrostatic charge on the blood, certain of its constituents, or items or particles in the blood. If it is desired to remove charged items from the blood, this may be done by opening a drain valve 198 on the flow line 199 from the conduit 193. The area A around the flow line 199's opening is charged so that the items to be removed are attracted thereto. Flow deflectors 201 assist in accumulating items to be removed. The flow line may be disposed through one of the windows.

Figure 11:
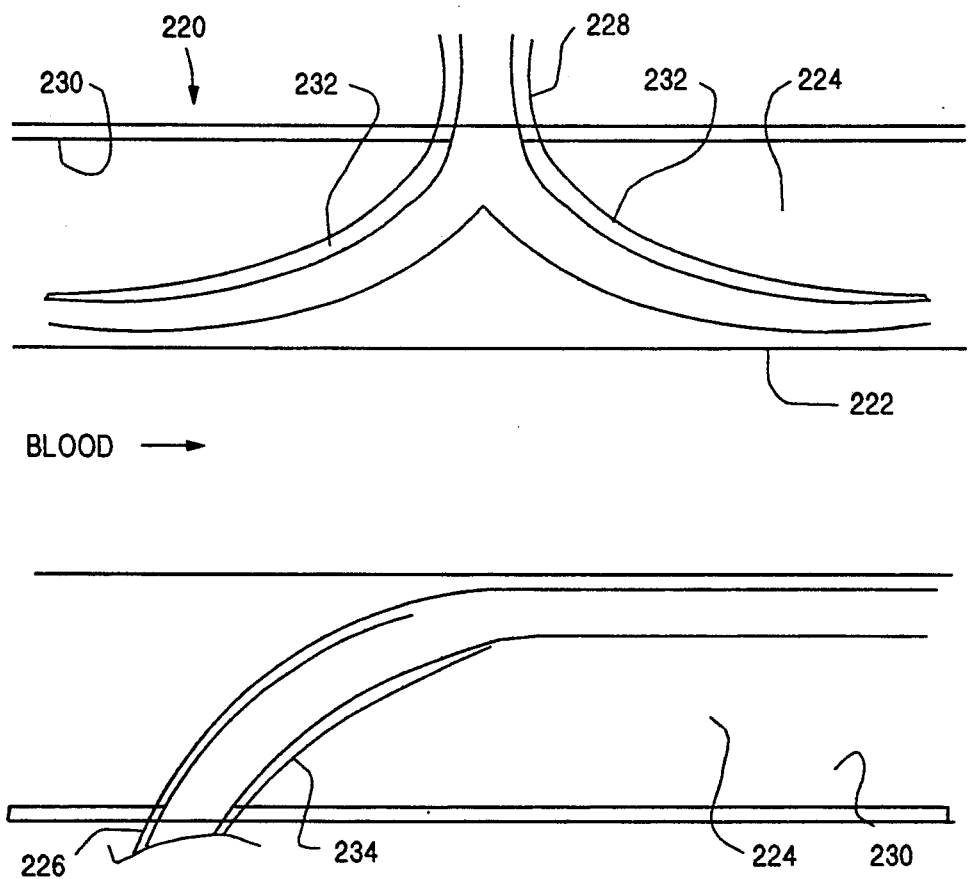
FIG. 11 is a side cross-sectional view of a device according to the present invention.

In a system 220 shown in FIG. 11, blood flows through a transparent conduit 222 which is surrounded by (or partially enclosed by) a transparent member 224. A fiber optic cable 226 with one or more fiber optic strands extends into the transparent member 224, but not into the transparent conduit 222. The fiber optic cable 226 is disposed within the transparent member 224 so that light (or other radiant energy) from the cable 226 may be directed into the blood flowing in the conduit 222. The transparent member 224 may be dispensed with if the cable 226 is adequately secured to or mounted on the conduit 222. Similarly a fiber optic cable 228 extends into the transparent member 224 and sub-parts thereof bearing one or more fiber optic strands are disposed adjacent (or on) the conduit 222 for radiating into the blood in the conduit 222. As shown opaque cladding to prevent light transmission may be used on the cables (226 and/or 228) and on the outer part of the transparent member 224 (cladding 230 on member 224; cladding 232 on cable 228; cladding 234 on cable 224). Blood coagulation problems are minimized with this system.

In conclusion, therefore, it is seen that the present invention and the embodiments disclosed herein are well adapted to carry out the objectives and obtain the ends set forth at the outset. Certain changes can be made in the methods and apparatuses without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to protect the invention broadly in whatever form its principles may be utilized. The present invention is, therefore, well adapted to carry out the objects and obtain the ends and advantages mentioned, as well as others inherent therein.

What is claimed is:

1. A method for extra-corporeally applying radiant energy to flowing blood flowing through a hollow tubular conduit, said radiant energy being blood reflectable, the method comprising
   introducing said radiant energy from a source through a first window at a first port in the conduit,
   directing said radiant energy to the flowing blood so that a portion of said radiant energy reflects back from the blood through the first window to a reflection member secured to the conduit,
   the reflection member directing a portion of said radiant energy back to the flowing blood through a second window at a second port in the conduit, and
   a portion of said radiant energy reflecting away from the blood back through the second window.

2. The method of claim 1 wherein the first and second windows are disposed on a first part of the conduit which is smaller in cross-sectional area than portions of the conduit on either side of the first portion so that velocity of blood flow is faster through the first part of the conduit than through the portions of the conduit on either side of the first part.

3. The method of claim 1 wherein:
   the conduit includes a transparent member secured adjacent the first and second windows,
   the radiant energy directed to and through a third window and a third port on the transparent member prior to passage through the first window,
   the reflection member secured to the transparent member,
   reflected radiant energy passing through the transparent member in going to and from the reflection member, and
   reflected radiant energy passing through the transparent member from the second window and passing through a fourth port and a fourth window on the transparent member.

4. The method of claim 1 wherein the radiant energy is electromagnetic radiation.

5. The method of claim 1 wherein the radiant energy is light.

6. The method of claim 5 wherein the light is infrared radiation and heats the blood.

7. The method of claim 5 wherein the light is a laser beam.

8. The method of claim 1 wherein only certain blood constituents are flowing through the conduit.

9. The method of claim 1 comprising also
   sensing the portion of the radiant energy reflected through the second window.

10. The method of claim 9 including
    analyzing the portion of the radiant energy reflected through the second window.

11. The method of claim 3 including
    sensing the portion of the radiant energy reflected through the fourth window and analyzing it.

12. The method of claim 1 wherein at least one of the window is a lens.

13. The method of claim 11 wherein the radiant energy is sound waves.

14. The method of claim 13 wherein the sound waves are ultrasonic or radio-frequency.

15. A method for extra-corporeally applying radiant energy to flowing blood flowing through a hollow tubular conduit, said radiant energy being blood reflectable, the method comprising
    introducing said radiant energy from a source through a first window at a first port in the conduit,
    directing said radiant energy to the flowing blood so that a portion of said radiant energy reflects back from the blood through the first window to a reflection member, secured to the conduit,
    the reflection member directing a portion of said radiant energy back to the flowing blood through a second window at a second port in the conduit,
    reflecting a portion of said radiant energy away from the blood back through the second window,
    the first and second windows are disposed on a first part of the conduit which is smaller in cross-sectional area than portions of the conduit on either side of the first portion so that velocity of blood flow is faster through the first part of the conduit than through the portions of the conduit on either side of the first part thereof, a transparent member secured adjacent the first and second windows,
    directing said radiant energy to and through a third window and a third port on the transparent member prior to passage through the first window,
    the reflection member secured to the transparent member,
    reflected radiant energy passing through the transparent member in going to and from the reflection member, and
    reflected radiant energy passing through the transparent member from the second window and passing through a fourth port and a fourth window on the transparent member, and
    sensing the portion of the radiant energy reflected through the fourth window and analyzing it.

16. A method for extra-corporeally radiating flowing blood with radiant energy, said radiant energy being blood reflectable,
    flowing the blood through an inner transparent flow conduit disposed within an outer conduit,
    directing said radiant energy thorough a window at a port on the outer conduit to the blood flowing in the inner conduit,
    directing said radiant energy to a beam splitter prior to encountering the flowing blood so that multiple energy rays are directed to the blood, and
    reflecting a portion of said radiant energy reflected from the blood to a reflective coating on an interior surface of the outer conduit which reflects a portion of said radiant energy back to the blood in the inner conduit.

17. The method of claim 16 wherein the radiant energy is electromagnetic radiation.

18. The method of claim 16 wherein the radiant energy is light.

19. The method of claim 17 wherein the light is a laser beam.

20. The method of claim 18 wherein the light is ultraviolet radiation.

21. The method of claim 16 wherein the radiant energy is infrared radiation which heats the blood.

22. The method of claim 16 wherein the window is a lens.

* * * * *